US009149238B2

(12) United States Patent
Watkins

(10) Patent No.: US 9,149,238 B2
(45) Date of Patent: Oct. 6, 2015

(54) FOOT-ACTIVATED CONTROLLER FOR IMAGING SYSTEM

(75) Inventor: Marvin C. Watkins, Cincinnati, OH (US)

(73) Assignee: LIEBEL-FLARSHEIM COMPANY LLC, Hazelwood, MO (US)

(*) Notice: Subject to any disclaimer, the term of this patent is extended or adjusted under 35 U.S.C. 154(b) by 381 days.

(21) Appl. No.: 12/921,787

(22) PCT Filed: Mar. 5, 2009

(86) PCT No.: PCT/US2009/036097
§ 371 (c)(1),
(2), (4) Date: Sep. 10, 2010

(87) PCT Pub. No.: WO2009/114367
PCT Pub. Date: Sep. 17, 2009

(65) Prior Publication Data
US 2011/0013005 A1 Jan. 20, 2011

Related U.S. Application Data

(60) Provisional application No. 61/036,189, filed on Mar. 13, 2008.

(51) Int. Cl.
A61B 6/00 (2006.01)
A61B 1/00 (2006.01)
A61B 1/045 (2006.01)
G05G 1/30 (2008.04)
G05G 5/03 (2008.04)
G06F 19/00 (2011.01)
(Continued)

(52) U.S. Cl.
CPC .............. *A61B 6/00* (2013.01); *A61B 1/00039* (2013.01); *A61B 1/045* (2013.01); *A61B 6/463* (2013.01);
(Continued)

(58) Field of Classification Search
CPC ............ A61B 1/04; A61B 1/00; A61B 19/00; G02B 23/24; H04N 5/225; H04N 7/18
USPC .......................................... 348/77
See application file for complete search history.

(56) References Cited

U.S. PATENT DOCUMENTS 5,422,521 A * 6/1995 Neer et al. ................... 307/119
5,635,777 A 6/1997 Telymonde et al.
(Continued)

FOREIGN PATENT DOCUMENTS

JP 2002-58641 2/2002
JP 2002/058641 A * 2/2002

OTHER PUBLICATIONS

Machine Translation of JP 2002/058641 A, Feb. 2002, Itou.*

*Primary Examiner* — Jay Patel
*Assistant Examiner* — Frank Huang
(74) *Attorney, Agent, or Firm* — Marsh Fischmann & Breyfogle LLP

(57) ABSTRACT

A foot-activated controller that communicates with at least one medical device is disclosed. This controller may incorporate a number of features. Multiple displays may be positioned on the controller for depicting the functionality of its various actuators. "Tapping" or partially depressing an actuator may cause an output that is representative of its functionality to be generated on its corresponding controller display, while fully depressing an actuator may initiate execution of its assigned function. The function assigned to each of the various actuators may be programmed by an external computer that may communicate with the controller over an appropriate communication link and via a communication port on the controller. Different audible feedbacks may be assigned to the various actuators, for instance to provide an audible indication of the function being executed.

25 Claims, 7 Drawing Sheets

(51) Int. Cl.
G05G 5/05 (2006.01)
A61B 6/04 (2006.01)
A61G 13/02 (2006.01)

(52) U.S. Cl.
CPC ............... *A61B 6/464* (2013.01); *A61B 6/465* (2013.01); *A61B 6/467* (2013.01); *G05G 1/305* (2013.01); *G05G 5/03* (2013.01); *A61B 6/0457* (2013.01); *A61G 13/02* (2013.01); *G05G 5/05* (2013.01); *G06F 19/00* (2013.01); *G06F 19/3412* (2013.01)

(56) References Cited

U.S. PATENT DOCUMENTS

| | | | | |
|---|---|---|---|---|
| 5,760,323 | A | * | 6/1998 | Romero et al. ............. 84/470 R |
| 5,777,602 | A | * | 7/1998 | Schaller et al. ............... 345/157 |
| 5,883,615 | A | | 3/1999 | Fago et al. |
| 7,428,439 | B1 | * | 9/2008 | Reynolds et al. ............... 700/17 |
| 7,675,430 | B2 | * | 3/2010 | Warner et al. ................ 340/12.5 |
| 2004/0138569 | A1 | | 7/2004 | Grunwald et al. |
| 2006/0074405 | A1 | | 4/2006 | Malackowski et al. |
| 2006/0090990 | A1 | | 5/2006 | Blaha et al. |

* cited by examiner

FOOT-ACTIVATED CONTROLLER FOR IMAGING SYSTEM

RELATED APPLICATIONS

This patent application is a U.S. National Stage of PCT/US2009/036097 filed on 5 Mar. 2009, which claims priority to and is a non-provisional application of U.S. provisional application Ser. No. 61/036,189 filed on 13 Mar. 2008 and entitled "FOOT-ACTIVATED CONTROLLER FOR IMAGING SYSTEM."

FIELD OF THE INVENTION

The present invention generally relates to the field of imaging systems that utilize imaging equipment and a movable table and, more particularly, to foot-activated controllers for such imaging systems.

BACKGROUND

Medical imaging systems exist that utilize an adjustable patient table and appropriate imaging equipment. One such imaging system is commonly referred to as a "urology table." Urology tables are used to perform various urology procedures. It is common for these types of medical imaging systems to utilize foot-activated controllers for communicating with the movable patient table and the imaging equipment. One foot-activated controller is typically provided for communicating with the movable patient table, while a separate foot-activated controller is typically provided for communicating with the imaging equipment.

Known foot-activated controllers for the patient table incorporate a number of pedals or switches for controlling the position of the patient table. Patient tables for urology applications typically are movable in each of a vertical dimension, as well as longitudinal and lateral dimensions within a reference plane that at least generally coincides with a supporting surface of the patient table. These tables may also be tilted about a horizontal axis (e.g., to raise the patient's head and simultaneously lower the patient's feet; to lower the patient's head and simultaneously raise the patient's feet). Known foot-activated controllers for the imaging equipment incorporate a number of pedals or switches for controlling various aspects of the image acquisition function.

SUMMARY

A first aspect of the present invention is embodied by a medical system, which includes a first medical device and a controller. The controller is foot-activated and is operatively interconnected or is able to communicate with the first medical device (e.g., the controller could communicate with more than one medical device). A plurality of actuator groups and a separate controller display for each actuator group are each incorporated by the controller. Each actuator group includes at least one actuator.

A second aspect of the present invention is embodied by a medical system, which includes a first medical device, a controller, and a display. The controller is foot-activated and is operatively interconnected or is able to communicate with the first medical device (e.g., the controller could communicate with more than one medical device). The controller includes at least one actuator. Moving an actuator from an inactive position to an intermediate position presents a function of this actuator on at least one display. Moving an actuator to its corresponding active or actuating position (e.g., from its corresponding intermediate position) initiates the execution of the function associated with the actuator. An actuator proceeds through its corresponding intermediate position moving from its inactive position to its actuating position.

A third aspect of the present invention is embodied by a medical system, which includes a first medical device, a controller, and a display. The controller is foot-activated and is operatively interconnected or is able to communicate with the first medical device (e.g., the controller could communicate with more than one medical device). The controller includes at least one actuator. Moving an actuator to an active or actuating position initially presents a function of this actuator on at least one display, but does not initiate the execution of the associated function. However, maintaining an actuator at its corresponding active or actuating position for at least a certain period of time (e.g., about ½ to 1 second) initiates the execution of the function associated with the actuator.

A fourth aspect of the present invention is embodied by a medical system, which includes a first medical device and a controller. The controller is foot-activated and is operatively interconnected or is able to communicate with the first medical device (e.g., the controller could communicate with more than one medical device). Additional components of the controller include at least one actuator, programmable logic that is operatively interconnected with at least one actuator, and a first communication port that is operatively interconnectable or is able to communicate with the programmable logic.

A fifth aspect of the present invention is embodied by a medical system, which includes a first medical device and a controller. The controller is foot-activated and is operatively interconnected or is able to communicate with the first medical device (e.g., the controller could communicate with more than one medical device). Additional components of the controller include a plurality of actuators that in turn includes first and second actuators, a first audible feedback that is associated with an actuation of the first actuator, and a second audible feedback associated with an actuation of the second actuator. The first and second audible feedbacks differ from each other in at least some respect.

A sixth aspect of the present invention is embodied by a medical system, which includes a first medical device and a controller. The controller is foot-activated, is operatively interconnected or is able to communicate with the first medical device (e.g., the controller could communicate with more than one medical device), and includes at least one actuator. A movement of an actuator at least generally toward its corresponding actuating position generates at least two feedbacks.

A seventh aspect of the present invention is embodied by a medical system, which includes an imaging assembly, a table, a table positioner, and a controller. The table positioner interacts with the table, while the controller is foot-activated and is operatively interconnected or is able to communicate with at least one of the imaging assembly and the table positioner. Additional components of the controller include at least one actuator and programmable logic. At least one actuator is operatively interconnected or is able to communicate with the programmable logic. The programmable logic utilizes at least two different actuator profiles. Each actuator profile includes an assignment of a function to at least one actuator (and thereby encompassing including a functional assignment for each such actuator).

An eighth aspect of the present invention is embodied by a medical system, which includes a first medical device, a controller, a display or monitor, and control logic. The controller is foot-activated, includes at least one actuator, and is operatively interconnected with the first medical device in any appropriate manner. The control logic is configured to present a first anatomical image on a first display, where this first anatomical image is from an ongoing medical procedure that utilizes the medical system in at least some respect. The control logic is further configured to simultaneously present a functional identifier on this same first display along with the noted first anatomical image, where this functional identifier conveys in any appropriate manner the function of an actuator from the foot-activated controller.

Various refinements exist of the features noted in relation to each of the above-noted first through the eighth aspects of the present invention. Further features may also be incorporated in each of the above-noted first through the eighth aspects of the present invention as well. These refinements and additional features may exist individually or in any combination in relation to each of the first through the eighth aspects. That is, each of the following features that will be discussed is not required to be used with any other feature or combination of features unless otherwise specified.

Each of the first through the eighth aspects may be used individually or may be combined in any appropriate manner. For instance, the controller utilized by each of the second through the eighth aspects may incorporate a plurality of actuator groups and a separate controller display for each actuator group, where each actuator group includes at least one actuator all in accordance with the first aspect. Any appropriate number of actuator groups may be utilized by the controller. In one embodiment, the controller incorporates three actuator groups. Each actuator group may include any appropriate number of actuators, including having an actuator group defined by a single actuator. One or more of the actuator groups may utilize the same number of actuators, one or more of the actuator groups may utilize a different number of actuators, or both. In one embodiment, each actuator group utilizes two actuators. Each actuator may be of any appropriate size, shape, configuration, and/or type (including where one or more of the actuators are of the same type/configuration, where one or more of the actuators are of a different type/configuration, or both).

The various controller displays that may be utilized by the controller may be of any appropriate size, shape, configuration, and/or type (e.g., in the form of LCDs or "liquid crystal displays"). Multiple controller displays that may be provided on the controller may be disposed in any appropriate arrangement. In one embodiment, each controller display is located a least generally in proximity to its corresponding actuator group. Since each actuator group could include a single actuator, having a separate controller display for each actuator of the controller is encompassed by the present invention.

A functionality associated with a particular actuator group may be presented on its corresponding controller display, on any other appropriate display(s) (e.g., one or more monitors being utilized by an imaging system), or both. In one embodiment, the function of each individual actuator in a particular actuator group may be presented on the corresponding controller display at least at some point in time. Consider the case where multiple actuators define an actuator group. The function of each actuator could be separately presented on the corresponding controller display, the function of two or more actuators in a common actuator group could be simultaneously presented on the corresponding controller display, or both.

Any appropriate representation of the functionality associated with a particular actuator group may be output to its corresponding controller display, to any other appropriate display(s), or both. In one embodiment, a graphical representation of the functionality associated with the actuator group is presented on its corresponding controller display. This graphical representation may be of any appropriate size, shape, configuration, and/or type (e.g., one or more icons; a colored, moving image). In one embodiment, a textual description of the functionality associated with the actuator group is presented on its corresponding controller display.

The controller utilized by each of the first and fourth through the eighth aspects may be configured such that moving an actuator from an inactive position to an intermediate position presents a function of this actuator on at least one display, such that moving an actuator to its corresponding actuating position initiates the execution of the function associated with the actuator, and such an actuator proceeds through its corresponding intermediate position moving from its inactive position to its active or actuating position—all in accordance with the second aspect. A movement of an actuator from its inactive position to its intermediate position (which presents its function on at least one display) may be characterized as partially depressing the actuator, while a movement of an actuator to its active or actuating position (which initiates execution of the assigned function) may be characterized as completely depressing the actuator.

The controller utilized by each of the first and fourth through the eighth aspects may be configured such that moving an actuator to an active or actuating position initially presents a function of this actuator on at least one display without initiating the execution of the associated function, while maintaining an actuator at its corresponding active or actuating position for at least a certain period of time (e.g., about ½ to 1 second) does then initiate the execution of the function associated with the actuator—all in accordance with the third aspect. The amount of time that an actuator must be maintained in its active or actuating position before initiating the associated function (e.g., the magnitude of the delay) may be of any appropriate value, may be programmable in any appropriate manner, or both. The controller may be further configured such that the noted delay will not apply if a given actuator is re-activated within a certain period of time (e.g., within about 30 seconds, and which could be a programmable value of any appropriate magnitude) without any intervening actuation of another actuator. In this regard, consider the case where an actuator $A_1$ is moved to its active or actuating position, which displays its associated function, and is maintained in this position for the time required to initiate the execution of its associated function. If the actuator $A_1$ is thereafter moved back to an inactive position, and is thereafter once again moved back to its active or actuating position within a certain amount of time without having moved any other actuator to its active or actuating position in the interim (e.g., between the two adjacent-in-time actuations of the actuator $A_1$), the controller may be configured such that the noted delay will be suspended for purposes of this subsequent movement of the actuator $A_1$ to its active or actuating position—this second movement of the actuator $A_1$ to its active or actuating position may immediately initiate the execution of its associated function in this type of instance.

The controller utilized by each of the first through the third aspects and the fifth through the eighth aspects may be configured to include programmable logic that is operatively interconnected with at least one actuator, and a first communication port that is operatively interconnectable or is able to communicate with the programmable logic—all in accordance with the fourth aspect. In such a medical system, a computer may be operatively interconnected with this first communication port by any appropriate communication link (e.g., wireless, computer cable). As such, the computer may be characterized as being a remote or external computer in relation to the foot-activated controller. This computer may be utilized to program the programmable logic (e.g., to assign a function to at least one actuator being utilized by the controller). Any appropriate computer may be utilized to communicate with the controller, including without limitation a laptop. The first communication port may be of any appropriate size, shape, configuration, and/or type (e.g., a wireless communication port using Radio Frequencies (RF), wireless Infrared, wireless ultrasound, or a serial or parallel communication port). Although an external or remote computer could be maintained in communication with the controller throughout operation of the controller with at least one medical device, the present invention also encompasses having such a computer only being in selective communication with the programmable logic via the first communication port (e.g., establishing communication only long enough to allow the computer to configure the programmable logic of the controller as desired/required).

The controller utilized by each of the first through the fourth aspects and the sixth and eighth aspects may be configured to include a plurality of actuators that in turn includes first and second actuators, a first audible feedback that is associated with an actuation of the first actuator, and a second audible feedback associated with an actuation of the second actuator, where the first and second audible feedbacks differ from each other in at least some respect—all in accordance with the fifth aspect. Having the first and second audible feedbacks be different from each other may be utilized to convey the existence of a functional difference between the first and second actuators. The first and second audible feedbacks may be of the same or different types. Each of the first and second audible feedbacks may be of any appropriate type such as an audible tone, a patterned tone, an audible message, an audible melody, or the like.

The controller utilized by each of the first through the fifth aspects and the seventh and eighth aspects may be configured such that a movement of an actuator at least generally toward its corresponding actuating position generates at least two feedbacks—all in accordance with the sixth aspect. Each feedback that is generated in relation to a movement of an actuator at least generally toward its corresponding actuating position may be of any appropriate type, including without limitation visual, audible, or both. Any visual feedback may be presented at any location or combination of locations, such as on a controller display, on a monitor of one or more computers associated with the medical system (e.g., a monitor associated with an imaging assembly), or both.

The medical system of each of the first through the sixth and eighth aspects may include an imaging assembly, a table, and a table positioner, where the table positioner interacts with the table, where the controller is operatively interconnected or is able to communicate with at least one of the imaging assembly and the table positioner, where this controller includes at least one actuator and programmable logic, where at least one actuator is operatively interconnected or is able to communicate with the programmable logic, where the programmable logic utilizes at least two different actuator profiles, and where each actuator profile includes an assignment of a function to at least one actuator—all in accordance with the seventh aspect.

The medical system of each of the first through the seventh aspects of the present invention may further include control logic. This control logic may be configured to present a first anatomical image on a first display or monitor, where this first anatomical image is from an ongoing medical procedure that utilizes the medical system in at least some respect. The control logic may be further configured to simultaneously present a functional identifier on this same first display along with the noted first anatomical image, where this functional identifier conveys the function of an actuator from the foot-activated controller. The first anatomical image may be acquired by any appropriate imaging technology. The functional identifier may convey the function of an actuator from a foot-activated controller in any appropriate manner (e.g., textually, graphically, or a combination thereof).

The medical system of the present invention may be utilized for any appropriate application. In one embodiment and where an imaging assembly is being utilized, the medical system is used for a medical application (e.g., for performing one or more urology procedures). Any appropriate imaging equipment may be utilized by the medical system, including without limitation one or more components for providing an imaging functionality such as x-ray, tomography, fluoroscopy, endoscopy, and any combination thereof.

Any table that is incorporated by the medical system of the present invention may be movable in any appropriate manner and/or in any appropriate dimension or combination of dimensions. The table may be moved in each of first and second directions within a reference plane that at least generally coincides with a supporting surface of the table. These two different directions may be orthogonal to each other—for instance one defining a longitudinal dimension or longitudinal axis (e.g., coinciding with a height dimension of a patient lying on the table, or coinciding with a dimension in which the patient's head and feet are spaced when lying on the table) and the other defining a lateral dimension or axis (e.g., coinciding with a dimension in which a patient's shoulders would be spaced if the patient were to lie on his/her back on the table in the above-noted manner). The longitudinal dimension or axis may coincide with the long axis of the supporting surface of the table, while the lateral dimension or axis may coincide with the short axis of the supporting surface of the table.

Another motion that the table may undergo is in the vertical dimension—a motion that changes the elevation of the table (and including the entirety of its supporting surface). Yet another type of motion that may be utilized for the table is a movement at least generally about a first axis. This first axis is subject to a number of characterizations, which apply individually and in any appropriate combination. For instance, the first axis may be horizontally disposed, may extend in the lateral dimension, or both. In one embodiment, the lateral dimension of the supporting surface of the table is maintained parallel to horizontal. Movement of the table at least generally about the first axis may be characterized as a tilting of the table. The angle at which the table is disposed relative to horizontal (e.g., the angle between the longitudinal axis of the table and horizontal) may be referred to as a "tilt angle." Tilting of the table may be undertaken to raise the patient's head and simultaneously lower the patient's feet, may be undertaken to lower the patient's head and simultaneously raise the patient's feet, or both.

Moving an actuator of the foot-activated controller to its active or actuating position may initiate any appropriate function or combination of functions in relation to the associated medical system. Each actuator of the foot-activated controller may be of any appropriate size, shape, configuration, and/or type (e.g., a pedal). Multiple actuators of the foot-activated controller may be disposed in any appropriate arrangement. Each actuator of the foot-activated controller may undergo any appropriate motion or combination of motions in moving to its active or actuating position, unless otherwise noted. Any appropriate number of actuators may be utilized by a foot-activated controller in the case of the present invention. In the case where a foot-activated controller does include a plurality of actuators, any appropriate number of its actuators may include any of the above-noted features discussed in relation to "an actuator," "at least one actuator", or the like, individually or in any combination. Therefore, each actuator of a foot-activated controller in the case of the present invention could include any of the above-noted features, individually or in any combination, although such is not a requirement of the present invention.

DETAILED DESCRIPTION

Figure 1:
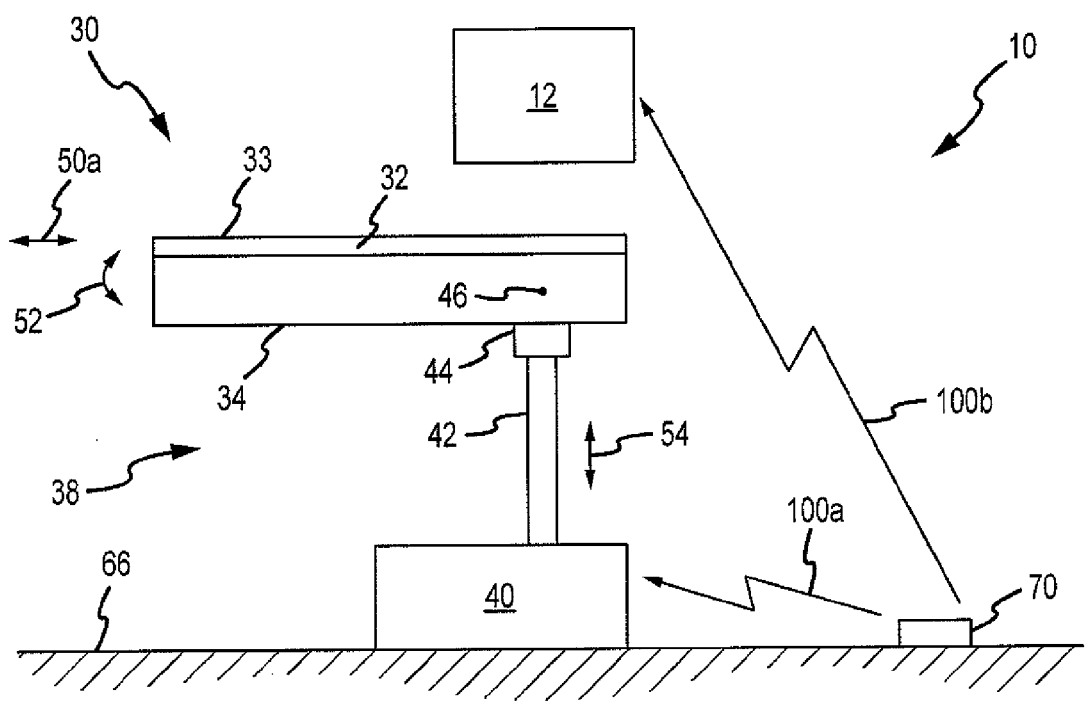
FIG. 1 is a schematic of one embodiment of an imaging system that uses a foot-activated controller.

One embodiment of an imaging system is illustrated in FIG. 1 and is identified by reference numeral 10. The imaging system 10 may be used for any appropriate application, including without limitation a medical application. Therefore, the imaging system 10 may be referred to as a medical imaging system 10.

The medical imaging system 10 includes an imaging assembly 12 and a table assembly 30, each of which may be of any appropriate size, shape, configuration, and/or type. The imaging assembly 12 may include any appropriate imaging equipment and any related components (e.g., for providing an x-ray functionality (e.g., acquiring an x-ray image), for providing a tomography functionality (e.g., acquiring a tomography image), for providing a fluoroscopy functionality (e.g., acquiring a fluoroscopy image), for providing an endoscopy functionality (e.g., acquiring an endoscopic image), and any combination thereof). Although the medical imaging system 10 may be configured for any appropriate medical application, in one embodiment the medical imaging system 10 is adapted for performing/facilitating the performance of one or more urology procedures.

The table assembly 30 may include a table or a tabletop 32, a table tub 34, and a table positioner 38. The table 32 may be moved relative to the table tub 34 by the table positioner 38 in each of first and second directions within a reference plane that at least generally coincides with a supporting surface 33 of the table 32. Double-headed arrow 50a in FIG. 1 represents one direction in which the table 32 may be moved relative to the table tub 34 within this reference plane, and which may define a longitudinal dimension or axis (e.g., coinciding with or defining the long axis of the supporting surface 33 of the table 32). The table 32 may also be moved relative to the table tub 34 in a direction that is orthogonal to the view presented in FIG. 1, and which may define a lateral dimension (e.g., see FIG. 2, which includes one double-headed arrow 50a to define the noted longitudinal dimension or axis, and which includes another double-headed arrow 50b to define a lateral dimension or axis). A patient would typically lie head-to-toe in the longitudinal dimension (e.g., coinciding with double-headed arrow 50a) on the supporting surface 33 of the table 32. If the patient were lying on his/her back in this fashion, the patient's shoulders would be spaced in the lateral dimension (e.g., coinciding with double-headed arrow 50b).

The table positioner 38 may provide multiple movements or movement types for the table 32. The table positioner 38 may be configured to move the table 32 relative to the table tub 34 in the above-noted manner (e.g., in each of the longitudinal and lateral dimensions coinciding with double-headed arrows 50a, 50b, respectively). The table positioner 38 may be configured to collectively move the table 32 and the table tub 34 in the vertical dimension, and as indicated by the double-headed arrow 54 (e.g., up and down relative to a floor 66, which may support one or more components of the medical imaging system 10). The table positioner 38 may be configured to collectively move the table 32 and the table tub 34 at least generally about an axis 46 that extends in the lateral dimension, that is horizontally disposed, or both, and as indicated by the double-headed arrow 52. This type of motion may be characterized as changing an angle between horizontal and the longitudinal dimension or axis 50a of the supporting surface 33 of the table 32. Another characterization of this motion is that it is a "tilting" of the table 32, for instance a "longitudinal tilting" of the table 32 (e.g., raising the head and simultaneously lowering the feet of the patient; lowering the head and simultaneously raising the feet of the patient). Therefore, the axis 46 may be referred to as a "tilt axis 46." The tilt axis 46 may be disposed at any appropriate location in the vertical dimension (e.g., double-headed arrow 54) and at any appropriate location in the longitudinal dimension (e.g., double-headed arrow 50a) of the table 32.

The table positioner 38 may be of any appropriate size, shape, configuration, and/or type to move the table 32 in any desired manner. In the illustrated embodiment, the table positioner 38 includes a base 40 that is disposed on the floor 66. The table positioner 38 utilizes a column 42 (e.g., the shaft of an appropriate cylinder) that may be both extended and retracted to raise and lower, respectively, the table 32 in the vertical dimension (e.g., to move the table 32 along an axis corresponding with the double-headed arrow 54). A joint 44 of any appropriate type allows the table positioner 38 to move the table 32 at least generally about the tilt axis 46. Part of the table positioner 38 (not shown) may be located within the table tub 34 or otherwise to move the table 32 relative to the table tub 34 in the above-noted longitudinal and lateral dimensions (e.g., in accordance with the two double-headed arrows 50a-b shown in FIG. 2).

The medical imaging system 10 of FIG. 1 includes a foot-activated controller 70 for controlling one or more aspects of the operation of at least one of, and including both of, the imaging assembly 12 and the table positioner 38. Therefore, the foot-activated controller 70 may be referred to as a multi-function controller. In any case, any appropriate communication link 100a may exist between the foot-activated controller 70 and the table positioner 38. Similarly, any appropriate communication link 100b may exist between the foot-activated controller 70 and the imaging assembly 12. The communication links 100a, 100b may be of a common or different type. In one embodiment, each communication link 100a, 100b is a wireless communication link.

Figure 2:
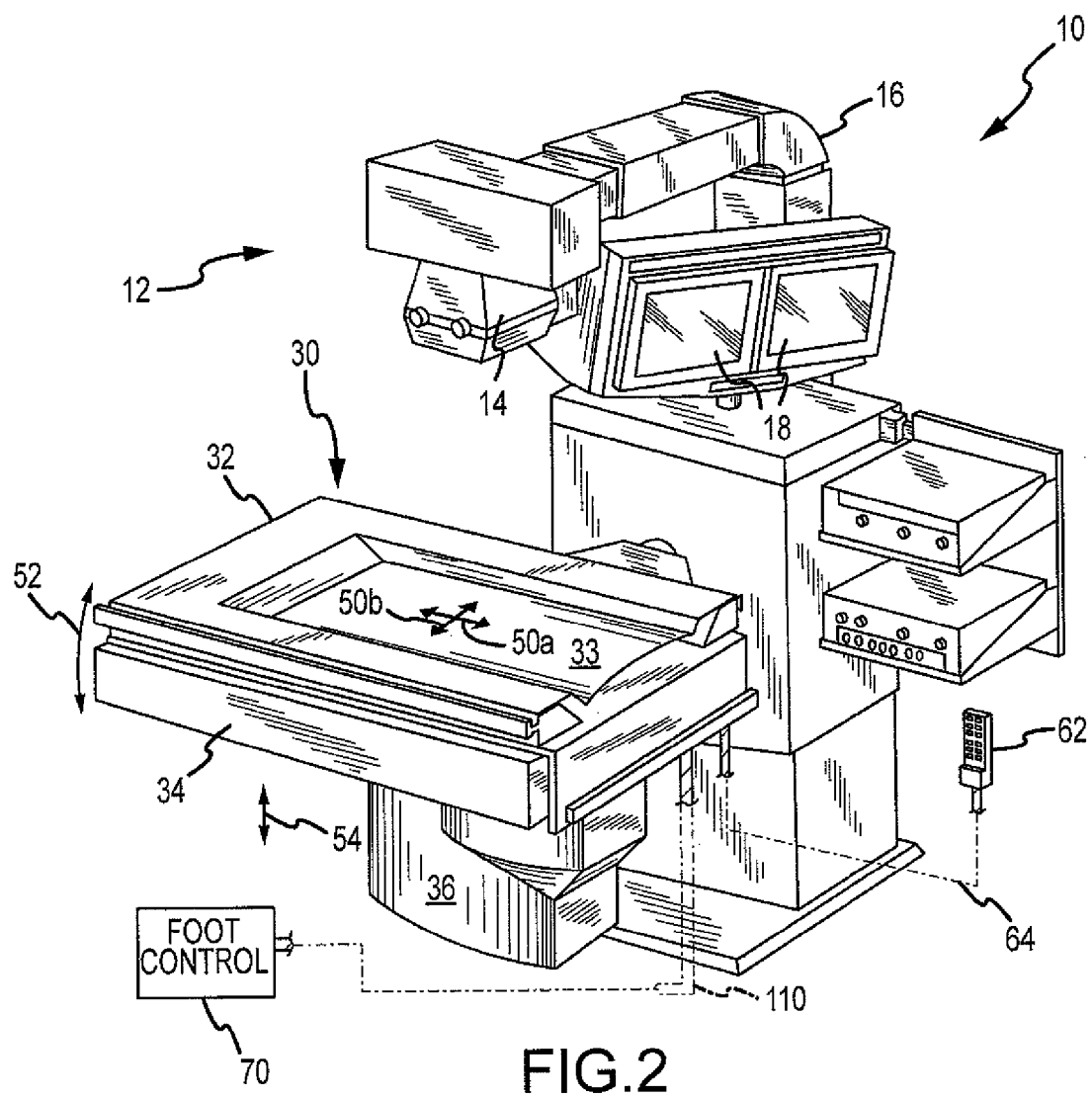
FIG. 2 is a more detailed view (perspective) of the imaging system of FIG. 1.

A more detailed view of the medical imaging system 10 is presented in FIG. 2. Here the imaging assembly 12 includes camera equipment 14 (e.g., for acquiring an x-ray image, for acquiring a tomography image, for acquiring a fluoroscopy image, for acquiring an endoscopic image, and any combination thereof), a support arm 16 for the camera equipment 14, and one or more monitors 18 (two shown) for displaying an acquired image. The lower portion of the table tub 34 is attached to a pedestal 36 in the FIG. 2 configuration. The table positioner 38 is not shown in FIG. 2, but is able to move the table 32 relative to the table tub 34 in each of the longitudinal and lateral dimensions (double-headed arrows 50a-b), is able to collectively move the table 32 and table tub 34 in the vertical dimension (double-headed arrow 54), and is able to collectively and longitudinally tilt the table 32 and table tub 34 at least generally about the tilt axis 46 (double-headed arrow 52).

The foot-activated controller 70 is operatively interconnected with each of the table positioner 38 and the imaging assembly 12 by a communication link 100. In accordance with the foregoing, the communication link 100 may be of any appropriate type (e.g., wireless). A separate communication link 100 may be provided between the foot-activated controller 70 and each of the table positioner 38 and the imaging assembly 12 or otherwise. The medical imaging system 10 may also include one or more hand-activated controllers 62, where each such hand-activated controller 62 is operatively interconnected with at least one of the table positioner 38 and the imaging assembly 12 by a communication link 64. Each such communication link 64 may be of any appropriate type (e.g., wireless). A separate communication link 64 may be provided between any particular hand-activated controller 62 and each of the table positioner 38 and the imaging assembly 12 or otherwise. A separate hand-activated controller 62 could also be provided for each of the table positioner 38 and the imaging assembly 12 (not shown).

Figure 3:
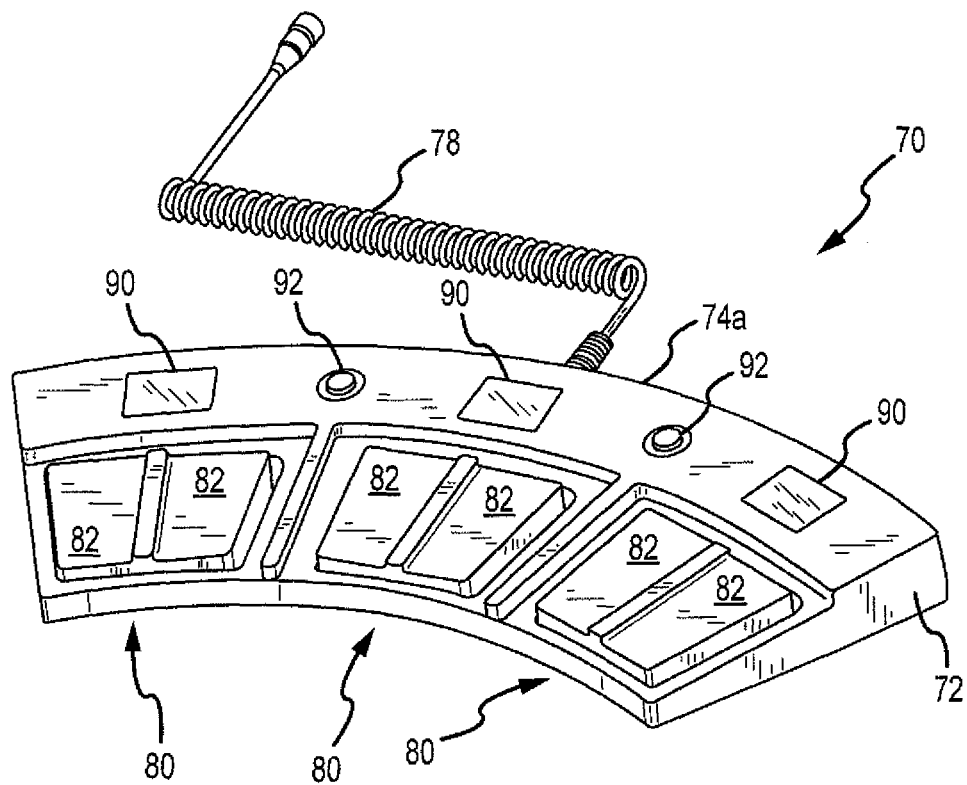
FIG. 3 is a perspective view of one embodiment of a foot-activated controller that may be used by the imaging systems of FIGS. 1 and 2.

One embodiment of the foot-activated controller 70 is illustrated in more detail in FIG. 3. The foot-activated controller 70 includes a housing or base 72 which may be disposed upon the floor 66, which may be of any appropriate size, shape, and/or configuration, and which may be formed from any appropriate material or combination of materials. A surface 74a of the housing 72 incorporates at least one group 80 of pedals or actuators 82. Any appropriate number of pedal groups 80 may be utilized by the foot-activated controller 70. Each pedal group includes 80 at least one pedal or actuator 82. Each pedal group 80 may include any appropriate number of pedals 82, including were each pedal group 80 includes the same number of pedals 82, as well as where at least one pedal group 80 utilizes a different number of pedals 82 that at least one other pedal group 80. In the illustrated embodiment, there are three pedal groups 80, and each pedal group 80 includes two pedals 82.

The individual pedals 82 may be of any appropriate size, shape, configuration, and/or type. In the illustrated embodiment, each pedal group 80 is in the form of a left/right rocker switch. Other "switch" configurations may be appropriate for each pedal 82. Each pedal 82 may be of the same "switch configuration" or otherwise. Any appropriate function or combination of functions may be initiated by activating a particular pedal 82.

In one embodiment, each of the pedals 82 in the same pedal group 80 provides at least somewhat of a related function. Consider the case where the foot-activated controller 70 is being used to control the motion of the table 32 for the medical imaging system of FIGS. 1-2. One pedal group 80 may be utilized to control the position of the table 32 in the vertical dimension and coinciding with the double-headed arrow 54 in FIGS. 1 and 2 (e.g., one pedal 82 in this pedal group 80 being used to raise the table 32, and the other pedal 82 in this pedal group 80 being used to lower the table 32). One pedal group 80 may be utilized to control the tilt angle of the table 32 and coinciding with the double-headed arrow 52 in FIGS. 1 and 2 (e.g., one pedal 82 in this pedal group 80 being used to raise the patient's head and simultaneously lower the patient's feet (e.g., move the table 32 at least generally about the tilt axis 46 in one direction), and the other pedal 82 in this pedal group 80 being used to lower the patient's head and simultaneously raise the patient's feet (e.g., move the table 32 at least generally about the tilt axis 46 in the opposite direction)). One pedal group 80 may be utilized to control the position of the table 32 in the lateral dimension and coinciding with the double-headed arrow 50b in FIG. 2 (e.g., one pedal 80 in this pedal group 82 being used to move the table 32 at least generally away from the camera equipment 14 in the lateral dimension, and the other pedal 82 in this panel group 80 being used to move the table 32 at least generally toward the camera equipment 14 in the lateral dimension).

The upper surface 74a also incorporates a controller display 90 for each pedal group 80. Each controller display 90 may be of any appropriate size, shape, configuration, and/or type (e.g., a liquid crystal display or LCD). Generally, the function of at least one pedal 82 may be presented on the corresponding controller display 90 in a manner that will be discussed in more detail below. In one embodiment, the function of each pedal 82 in each pedal group 80 is simultaneously presented on the corresponding controller display 90 at a given time. In one embodiment, the function of a single pedal 82 is presented on its corresponding controller display 90 at a given time. Since each pedal group 80 could conceivably include a single pedal 82, the foot-activated controller 70 could provide a controller display 90 for each pedal 82. However and for the case where there are multiple pedals 82 that each provide at least somewhat of a common function (e.g., changing the position of the table 32 in the vertical dimension), it may be beneficial to include these pedals 82 in a common pedal group 80 and to utilize a single controller display 90 for this particular pedal group 80.

One or more additional switches 92 may be incorporated on the upper surface 74a of the foot-activated controller 70. Any appropriate number of switches 92 may be utilized, and each individual switch 92 may be disposed at any appropriate location. Each switch 92 may provide any appropriate function or combination of functions (e.g., turning on/off an image saving function; turning on/off room lights; brightening/dimming room lighting; turning on/off a power injector).

Figure 3A:
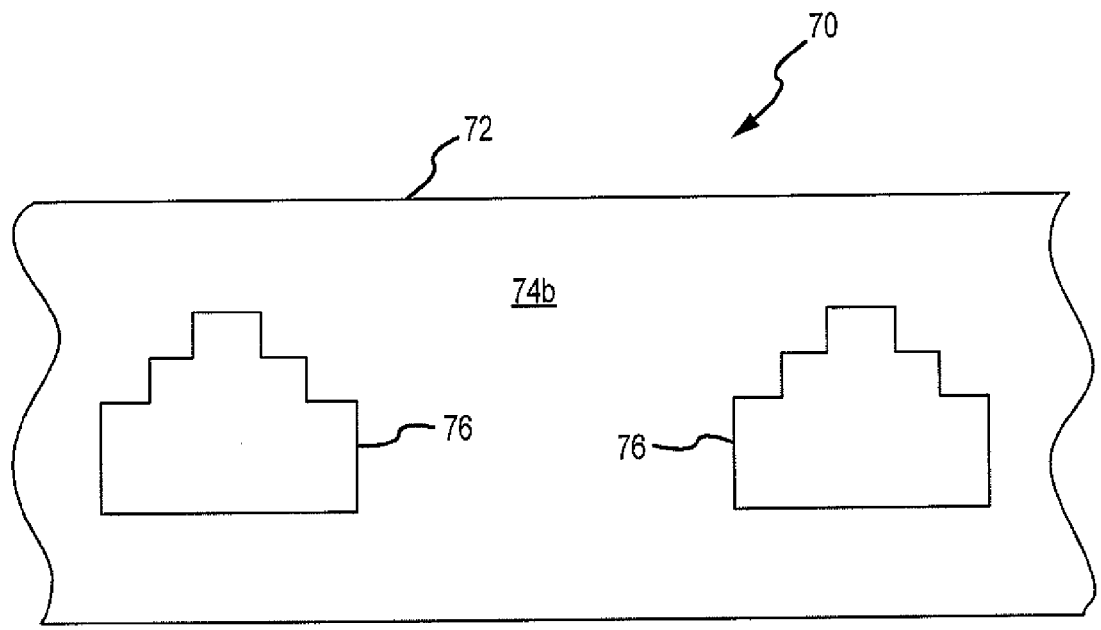
FIG. 3A is a plan view of a rear panel of the foot-activated controller of FIG. 3.

The foot-activated controller 70 may communicate in any appropriate manner with one or more medical devices (e.g., the imaging assembly 12 and/or table positioner 38 of the medical imaging system 10 of FIGS. 1-2), including without limitation wirelessly or via appropriate cabling, wiring, or the like. FIG. 3 illustrates a communication cable 78 that may be operatively interconnected with the foot-activated controller 70 and one or more medical devices. In this regard and referring now to FIG. 3A, a rear surface 74b of the housing or base 72 may include one or more communication ports 76. Each communication port 76 may be of any appropriate type (e.g., wireless, serial) and allows the foot-activated controller 70 to communicate with any appropriate device. One or more different types of communication ports 76 may be provided for the foot-activated controller 70, and each communication port 76 may be disposed at any appropriate location on the housing 72 of the foot-activated controller 70.

Figure 3B:
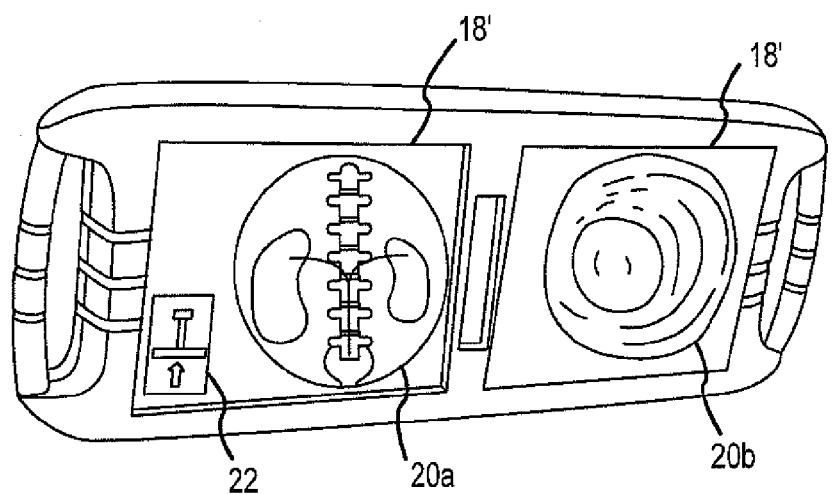
FIG. 3B is a perspective view of a pair of displays or monitors that may be used by the imaging system of FIGS. 1-2, where these monitors are presenting representative anatomical images from an ongoing medical procedure, and where one of these monitors is also presenting a representative functional identifier for a selected pedal of the foot-activated controller of FIG. 3.

An indication of the function(s) of a given pedal 82 of the foot-activated controller 70 may be presented on its corresponding controller display 90 as noted above. This indication may be of any appropriate size, shape, configuration, and/or type (e.g., textual, graphical, or a combination thereof), and may be referred to as a functional identifier. Each controller display 90 is again on or part of the foot-activated controller 70. The foot-activated controller 70 may be implemented to display a functional identifier at one or more additional locations. FIG. 3B illustrates such a situation, where a pair of displays or monitors 18' is each presenting a representative anatomical image 20a, 20b from an ongoing medical procedure. Each of the anatomical images 20a, 20b may be generated by any appropriate imaging technology (e.g., x-ray, endoscope), including where the anatomical images 20a, 20b are generated by the same type of imaging technology or by different imaging technologies as shown.

A functional identifier 22 may be presented on at least one monitor 18'. The functional identifier 22 in this instance is a graphical representation that conveys the function of a selected pedal 82 of the foot-activated controller 70 ("table up" (e.g., table 32) in the illustrated embodiment). How a pedal 82 of the controller 70 may be "selected" for purposes of ascertaining its associated function(s) will be discussed in more detail below. Each pedal 82 of the controller 70 may be a "selected" pedal 82 for purposes of conveying information on its associated function before actually executing this function. It should be appreciated that the monitors 18' shown in FIG. 3B may be used by any appropriate medical system, including the medical imaging system 10 of FIGS. 1-2. It should also be appreciated that any appropriate number of monitors 18' may be utilized by a given medical system, including where one or more monitors 18' are included in a common structure as shown in FIG. 3B, where one or more monitors 18' are contained within separate structures at different locations, or any combination thereof.

Figure 4A:
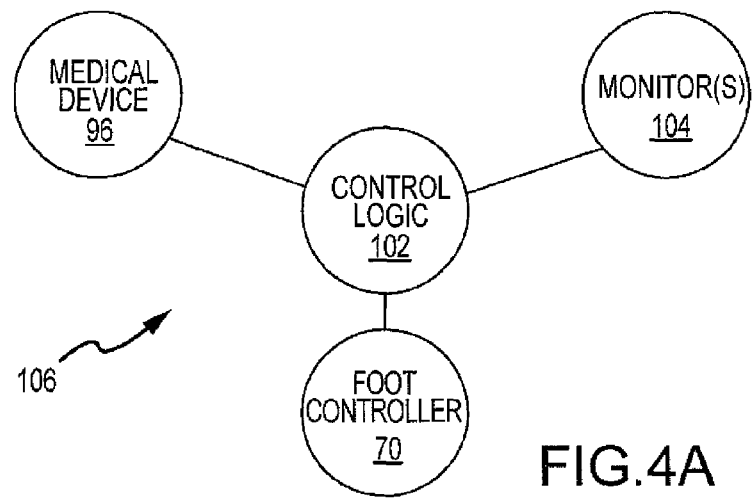
FIG. 4A is one embodiment of a functional schematic of a medical system that uses a medical device, at least one monitor, the foot-activated controller of FIG. 3, and control logic that is configured to present the type of output shown in FIG. 3B.

The foot-activated controller 70 may be used in relation to any appropriate medical system. FIG. 4A illustrates a functional schematic of a medical system 106 that includes at least one foot-activated controller 70, at least one medical device 96, at least one display or monitor 104, and control logic 102. The foot-activated controller 70 may be operatively interconnected with at least one medical device 96 in any appropriate manner, where each medical device 96 may be of any appropriate size, shape, configuration, and/or type. The control logic 102 may be of any appropriate form and/or configuration, for instance software, may be implemented or integrated in any appropriate manner, or both (e.g., implemented by software, hardware, firmware, and any combination thereof). In one embodiment, the functionality of the control logic 102 is provided by one or more processors of any appropriate size, shape, configuration, and/or type. In one embodiment, the functionality of the control logic 102 is provided by one or more computers of any appropriate size, shape, configuration, and/or type.

In the illustrated embodiment of FIG. 4A, each of the medical device 96, the monitor 104, and the foot-activated controller 70 are shown as being in operative communication with the control logic 102. This may be done through any appropriate arrangement and with the control logic 102 being of any appropriate configuration. For instance, the control logic 102 could be a single "structure," may be partitioned into a plurality of sectors or segments, may include one or more sectors or segments at different locations, or any combination thereof. In any case and in one embodiment, the control logic 102 may be configured to: 1) present at least one anatomical image 20a/20b (from an ongoing medical procedure) on at least one monitor 104 (e.g., monitor 18' of FIG. 3B); and 2) simultaneously present a functional identifier 22 along with at least one anatomical image 20a/20b on a common monitor 104, where the functional identifier 22 again somehow conveys the function of a selected pedal 82 of the foot-activated controller 70. Although the functional identifier 22 could at least partially "overlay" an anatomical image 20a/20b being simultaneously presented on the same monitor 104, the functional identifier 22 and any anatomical image 20a/20b being simultaneously presented on the same monitor 104 may be disposed in non-overlapping relation as shown in FIG. 3B.

Figure 4B:
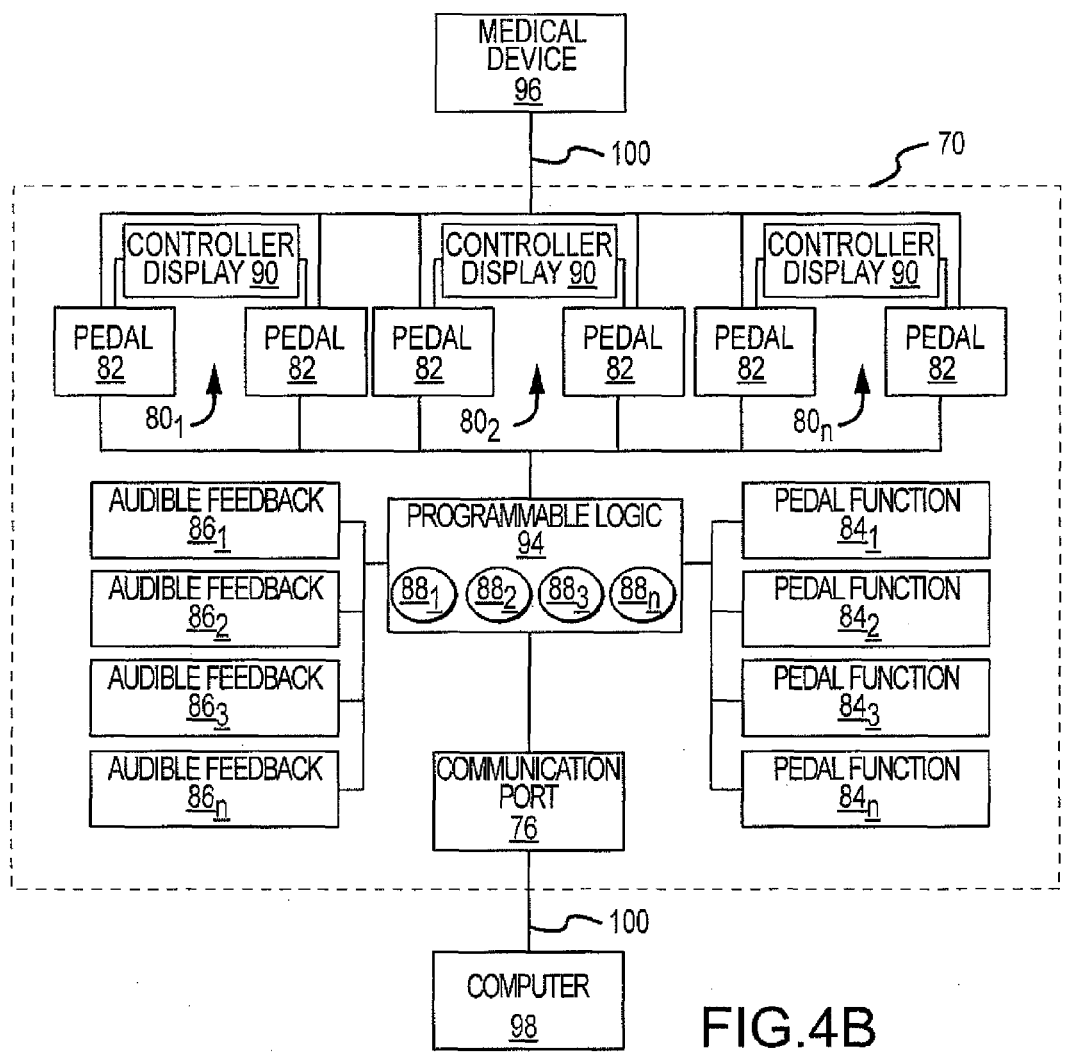
FIG. 4B is one embodiment of a functional schematic that may be utilized by the foot-activated controller of FIG. 3.

FIG. 4B presents a representative functional schematic that may be utilized by the foot-activated controller 70, and for the case where the foot-activated controller 70 is operatively interconnected with a medical device 96 (e.g., table positioner 38; imaging assembly 12) via an appropriate communication link 100 of any appropriate type (e.g., wireless, serial cable). The foot-activated controller 70 includes a programmable logic 94 which may be of any appropriate configuration. Generally, the logic 94 may be programmed using an external or remote computer 98 of any appropriate type (e.g., a laptop) via a communication link 100 of any appropriate type (e.g., wireless, serial cable), along with a communication port 76 of the foot-activated controller 70 that is operatively interconnected with the programmable logic 94. Each communication port 76 of the foot-activated controller 70 may communicate with its programmable logic 94 in any appropriate manner.

The various pedal groups 80 of the foot-activated controller 70 may be operatively interconnected with the programmable logic 94 in any appropriate manner. More generally, each of the various pedals 82 may be operatively interconnected with the programmable logic 94 in any appropriate manner. Any appropriate programming may be undertaken in relation to each pedal 82. Although each pedal 82 may be programmed, each of the pedals 82 may not be required for a given application/procedure, and therefore programming of any such unused pedals 82 may not be undertaken in each instance.

One or more pedal functions 84 may be stored in any appropriate manner and used to configure the programmable logic 94 of the foot-activated controller 70 of FIG. 4B. Any appropriate number of pedal functions 84 may be made available for assignment to each particular pedal 82. Generally, a pedal function 84 initiates a certain action upon its execution (e.g., activation of a pedal 82 having this assigned pedal function 84).

One or more audible feedbacks 86 may be stored in any appropriate manner and used to configure the programmable logic 94 of the foot-activated controller 70 of FIG. 4B. Any appropriate number of audible feedbacks 86 may be made available for assignment to each particular pedal 82. Each audible feedback 86 differs in at least some respect from the other audible feedbacks 86. Each audible feedback 86 may be of any appropriate type, for instance in the form of a tone, a pulsed tone, a voice message, a melody, or the like. Assigning a different audible feedback 86 to each pedal 82 may be used to identify each particular pedal 82 during use of the foot-activated controller 70.

Multiple pedal profiles 88 may be stored in relation to the foot-activated controller 70 of FIG. 4B. Each pedal profile 88 includes an assigned pedal function 84 and assigned audible feedback 86 for each pedal 82 that is to be used by the foot-activated controller 70 for a particular application/procedure. Any appropriate number of pedal profiles 88 may be stored, and may be accessed by personnel in any appropriate manner (e.g., through one of the switches 92 on the foot-activated controller 70).

Figure 5:
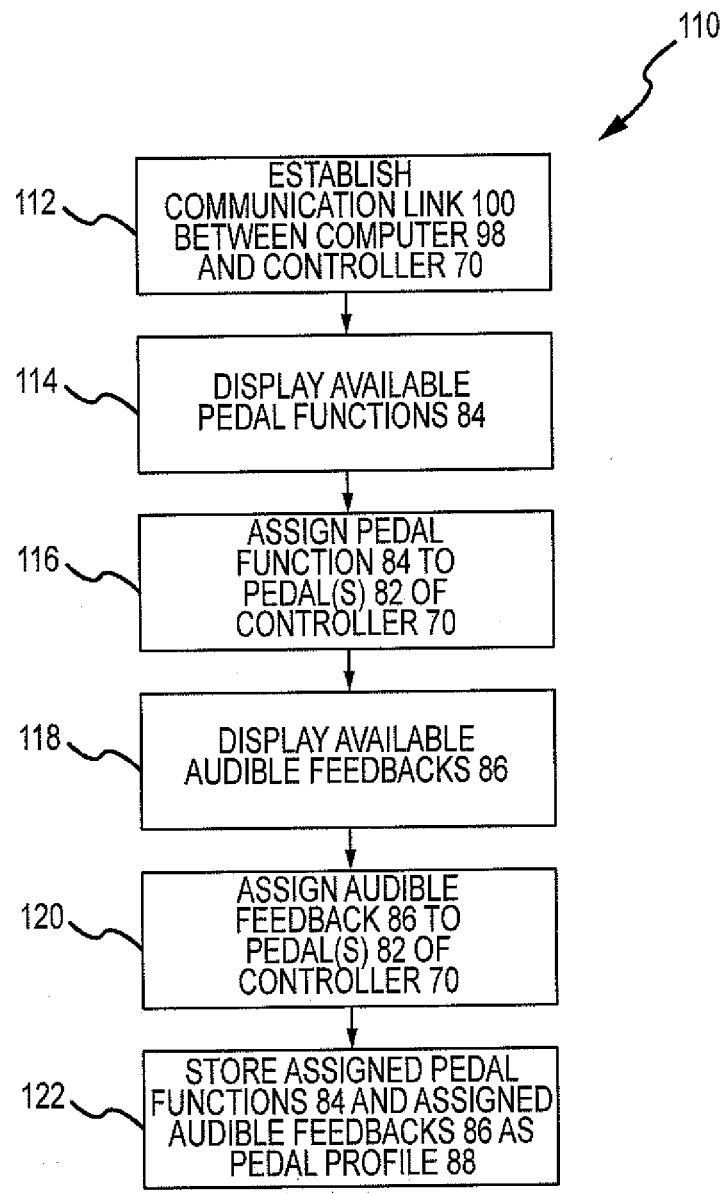
FIG. 5 is one embodiment of a programming protocol that may be utilized by the foot-activated controller of FIG. 3.

One embodiment of a protocol for programming the foot-activated controller of FIGS. 3-4 is illustrated in FIG. 5 and is identified by a reference numeral 110. The programming protocol 110 includes establishing a communication link 100 between an external or remote computer 98 and the foot-activated controller 70 (e.g., via an appropriate communication port 76 on the foot-activated controller 70). One or more pedal functions 84 may be displayed (e.g., on the computer 98) in any appropriate manner through execution of step 114. In one embodiment, a listing of all pedal functions 84 that are available for assignment to the pedals 82 may be presented on an appropriate display (e.g., via a drop-down menu). A pedal function 84 may be assigned to one or more of the pedals 82 of the foot-activated controller 70 (including each of the pedals 82) through execution of step 116.

One or more audible feedbacks 86 may be displayed (e.g., on the computer 98) in any appropriate manner through execution of step 118 of the programming protocol 110 of FIG. 5. In one embodiment, a listing of all audible feedbacks 86 that are available for assignment to the pedals 82 of the foot-activated controller 70 may be presented on an appropriate display (e.g., via a drop-down menu). An audible feedback 86 may be assigned to one or more of the pedals 82 of the foot-activated controller 70 (including each of the pedals 82) through execution of step 120. The assigned pedal functions 84 (step 116) and assigned audible feedbacks 86 (step 120) may be stored as a pedal profile 88 through execution of step 122. It should be appreciated that the assignment of the various function(s) to a particular pedal 82 may be undertaken in any appropriate order.

Figure 6:
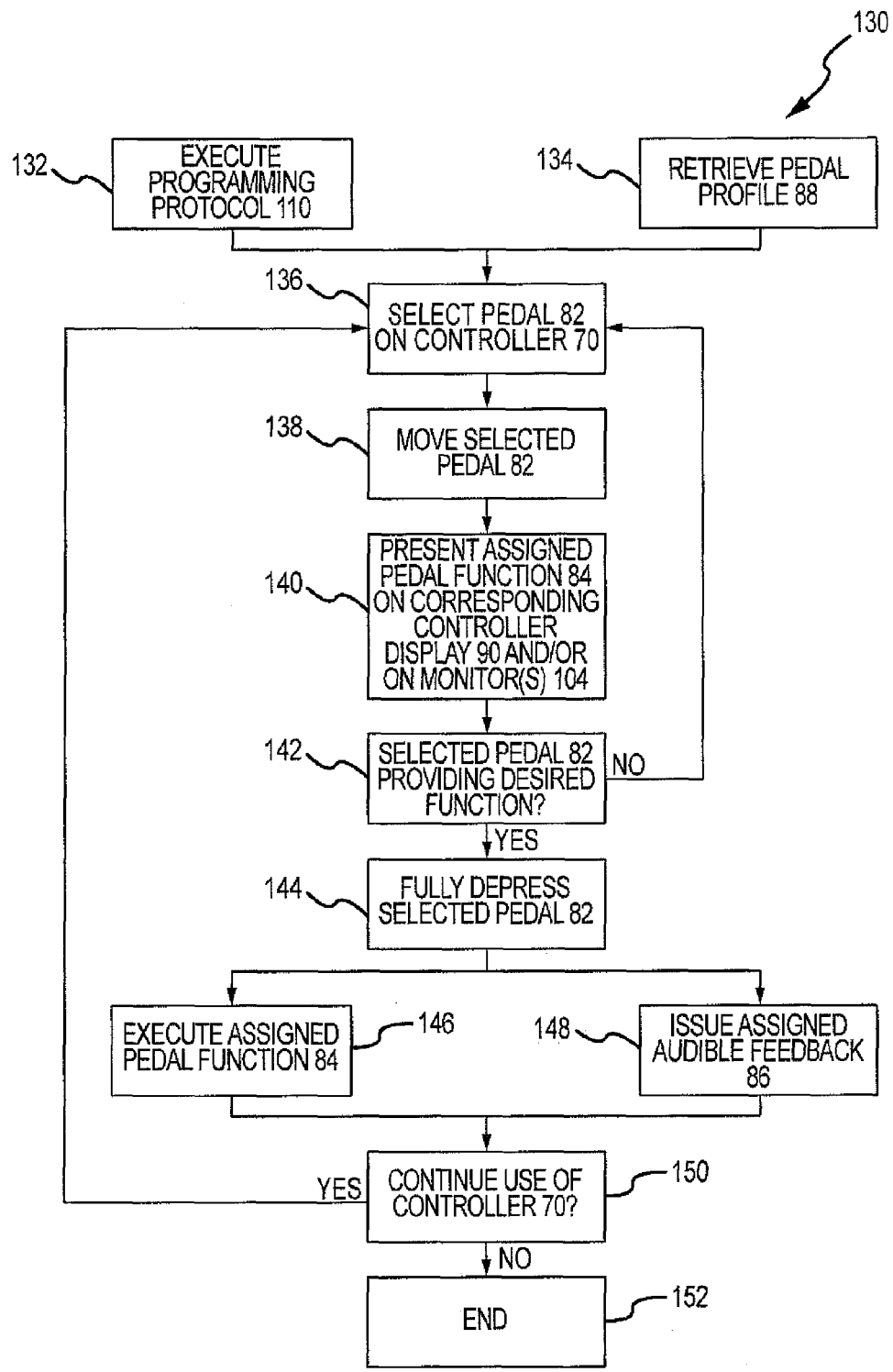
FIG. 6 is one embodiment of an operations protocol that may be utilized by the foot-activated controller of FIG. 3.

The foot-activated controller 70 of FIGS. 3 and 4B may be operated in accordance with an operations protocol 130 that is presented in FIG. 6. Other protocols may be appropriate. The operations protocol 130 accommodates executing the programming protocol 110 of FIG. 5 (step 132), as well as retrieving a stored pedal profile 88 (step 134). Steps 132 and 134 are each generally directed to the programmability for the pedals 82 of the foot-activated controller 70, although such may not be required in all instances. Once the desired pedal assignments have been realized in any appropriate manner, the foot-activated controller 70 may be used to control one or more aspects of the operation of at least one medical device 96 (FIG. 4B).

Step 136 of the operations protocol 130 of FIG. 6 is directed to selecting a pedal 82 for initiating the execution of a desired function. The operations protocol 130 is configured to provide operator feedback before the function of the selected pedal 82 is actually initiated. There are a number of options that may be employed to convey the function of a selected pedal 82 prior to actually executing its corresponding function. In the two instances to be addressed herein, the selected pedal 82 is moved in at least some fashion pursuant to step 138 of the operations protocol 130.

In one configuration of the operations protocol 130, step 138 entails partially depressing or "tapping" the selected pedal 82 (e.g., moving the selected pedal 82 from an inactive position to an intermediate position, and at least generally in a first direction). Once the selected pedal 82 is partially depressed in accordance with this option/configuration, the assigned pedal function 84 is presented on the corresponding controller display 90, on at least one monitor 104, or both, through execution of step 140 of the operations protocol 130. This functionality may be displayed at one or more locations and in any appropriate manner (e.g., graphically, pictorially, or any combination thereof). The functionality may be conveyed in any appropriate manner, including without limitation using one or more still images, using one or more moving images, using a single color, using multiple colors, or any combination thereof. In any case, this provides a visual feedback to the operator of the foot-activated controller 70. The audible feedback 86 that is assigned to the selected pedal 82 may also be issued at this time (not shown in FIG. 6, but from partially depressing or "tapping" a pedal 82). Therefore, the operations protocol 130 may be configured to provide multiple operator feedbacks regarding each pedal 82 of the foot-activated controller 70 before the assigned pedal function 84 is actually initiated.

Another option for conveying the function of a selected pedal 82 of the foot-activated controller 70 prior to actually executing its corresponding function, and in accordance with the operations protocol 130 of FIG. 6, entails incorporating a "delay" function in relation to each pedal 82 of the foot-activated controller 70. Instead of step 138 of the operations protocol 130 being a movement of a selected pedal 82 from an inactive position to an intermediate position, in this configuration of the operations protocol 130 step 138 entails moving the selected pedal 82 to its active or actuating position. Steps 140 and 142 of the operations protocol 130 are then executed in the above-noted manner and without initiating the corresponding function of the selected pedal 82. The above-noted audible feedback 86 may be issued at this time as well. In any case, only after the selected pedal 82 is maintained in its active or actuating position for a certain amount of time (e.g., about ½ to 1 second) will the corresponding function actually be initiated. The amount of time that the selected pedal 82 is required to be maintained in its active or actuating position before its corresponding function is initiated may be of any appropriate value, may be established/input in any appropriate manner, may be user programmable, or any combination thereof. The time between which the selected pedal 82 reaches its active or actuating position and when the associated function is actually initiated may be characterized as a delay.

In the event that the operator has inadvertently selected the wrong pedal 82 of the foot-activated controller 70 in accordance with either of the above-noted configurations, the operations protocol 130 of FIG. 6 allows another pedal 82 to be selected in the above-noted manner and without initiating its assigned pedal function 84 (e.g., via step 142, which returns control to step 136). Otherwise, the protocol 130 proceeds to execute the assigned pedal function 84 (step 146), to issue the assigned audible feedback 86 (step 148), or both. In the first-noted configuration of the operations protocol 130, prior to the execution of steps 146 and/or 150, the selected pedal 82 must be fully depressed or activated (e.g., by a movement of the selected pedal 82 to its active or actuating position and at least generally in the first direction—a movement of a pedal 82 from its inactive position to its active or actuating position will thereby pass through the noted intermediate position). Maintaining the selected pedal 82 in its active or actuating position throughout the associated delay alleviates the need for step 144 in the second-noted configuration.

Various procedures may of course require multiple actuations of one or more of the pedals 82 of the foot-activated controller 70. The operations protocol 130 accommodates for such scenarios through execution of step 150 and a return to step 136 for repetition in accordance with the foregoing. Otherwise, the operations protocol 130 may be terminated in any appropriate manner through execution of step 152. In the case where multiple actuations of one or more pedals 82 may be required, the second-noted configuration of the operations protocol 130 may be implemented to alleviate the "delay" associated with moving a selected pedal 82 to its active or actuating position. In this regard, consider the case where a first pedal 82 is moved to its active or actuating position, where its function is displayed for a certain period of time prior to initiating its associated function by maintaining the selected pedal 82 in its active or actuating position. Assuming that the first pedal 82 is then moved back to its inactive position after its corresponding function is executed, and that this same first pedal 82 is thereafter moved back to its active or actuating position within a predetermined amount of time (which may be of any appropriate value (e.g., about 30 seconds), which may be programmable in any appropriate manner, or both) without any of the other pedals 82 having been moved to their respective active or actuating position in the interim, this second (or any subsequent) movement of this first pedal 82 back to its active or actuating position may immediately initiate the execution of its corresponding function (i.e., the above-noted "delay" need not be implemented for this subsequent use of the noted first pedal 82 in this type of instance).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A medical imaging system, comprising:
   an imaging assembly;
   a table;
   a table positioner; and
   a controller operatively interconnected with at least one of said imaging assembly and said table positioner, wherein said controller is foot-activated and comprises:
   a housing;
   a plurality of actuator groups incorporated by said housing, wherein each actuator group of said plurality of actuator groups provides a different function in relation to every other said actuator group, wherein each said actuator group of said plurality of actuator groups comprises an actuator, wherein activation of each said actuator of each said actuator group initiates a corresponding function, wherein each said actuator incorporated by said housing occupies a different position on said housing, wherein said plurality of actuator groups comprises a first actuator group, and wherein said first actuator group comprises a plurality of said actuators; and
   a separate controller display for each said actuator group such that each said actuator group communicates with a different said controller display on said housing of said foot-activated controller, wherein as there are a plurality of said actuator groups there are then a plurality of said controller displays, wherein each said actuator of each said actuator group communicates with its corresponding said controller display such that said plurality of said actuators of said first actuator group communicate with a common said controller display and such that at least one other said actuator on said housing communicates with a different said controller display on the same said housing, wherein each said controller display is incorporated by said housing and each said controller display is positioned on a common surface of said housing, wherein a first movement of each said actuator of each said actuator group initiates presentation of an identification of its said corresponding function on its corresponding said controller display without initiating execution of its said corresponding function.

2. The medical imaging system of claim 1, wherein each said actuator group comprises two said actuators.

3. The medical imaging system of claim 1, wherein said plurality of actuator groups comprises three of said actuator groups.

4. The medical imaging system of claim 1, wherein a functionality of each said actuator group may be presented on its corresponding said controller display.

5. The medical imaging system of claim 1, wherein a graphical representation of a function of each said actuator group may be presented on its corresponding said controller display.

6. The medical imaging system of claim 5, wherein said graphical representation comprises a colored, moving image.

7. The medical imaging system of claim 1, wherein a textual description of a functionality of each said actuator group may be presented on its corresponding said controller display.

8. The medical imaging system of claim 1, further comprising a display, wherein an output on each said controller display may be simultaneously presented on said display.

9. The medical imaging system of claim 1, wherein moving each said actuator from an inactive position to an intermediate position presents-a said corresponding function of said actuator on said controller display, wherein moving each said actuator to an actuating position initiates said corresponding function of said actuator, and wherein each said actuator proceeds through said intermediate position while moving from said inactive position to said actuating position.

10. The medical imaging system of claim 1, wherein partially depressing each said actuator presents said corresponding function of said actuator on said controller display, and wherein fully depressing each said actuator initiates said corresponding function of said actuator.

11. The medical imaging system of claim 1, wherein moving each said actuator to an actuating position initially presents-a said corresponding function of said actuator on said controller display, and wherein maintaining each said actuator in said actuating position for a predetermined amount of time thereafter initiates an execution of said corresponding function of said actuator.

12. The medical imaging system of claim 1, wherein said controller further comprises:
   programmable logic operatively interconnected with each said actuator; and a first communication port operatively interconnected with said programmable logic.

13. The medical imaging system claim 12, further comprising:
   a computer; and
   a communication link extending between said computer and said first communication port on said controller.

14. The medical imaging system of claim 12, wherein said first communication port is selected from the group consisting of a wireless communication port using Radio Frequencies (RF), wireless Infrared, wireless ultrasound, and a serial or parallel communication port.

15. The medical imaging system of claim 12, wherein at least one function may be assigned to each said actuator through said first communication port.

16. The medical imaging system of claim 12, wherein each said actuator is programmable through said first communication port.

17. The medical imaging system of claim 1, wherein said controller comprises:
   said actuators on said housing comprising first and second actuators;
   a first audible feedback associated with actuation of said first actuator, and
   a second audible feedback associated with actuation of said second actuator, wherein said first and second audible feedbacks are different.

18. The medical imaging system of claim 17, wherein said first and second audible feedbacks are different to indicate a functional difference provided by an actuation of said first and second actuators.

19. The medical imaging system of claim 1, wherein a movement of said each said actuator toward an actuating position generates at least two feedbacks, wherein each said feedback is selected from the group consisting of a visual feedback and an audible feedback.

20. The medical imaging system of claim 1, wherein said controller further comprises programmable logic operatively interconnected with each said actuator, wherein said programmable logic comprises first and second actuator profiles, and wherein each of said first and second actuator profiles comprises a function assigned to each said actuator.

21. The medical imaging system of claim 1, wherein said imaging system is adapted for at least one urology application.

22. The medical imaging system of claim 1, wherein said imaging assembly comprises equipment selected from the group consisting of x-ray, tomography, fluoroscopy, endoscopy, and any combination thereof.

23. The medical imaging system of claim 1, wherein said table is movable in first and second directions within a first plane that coincides with a supporting surface of said table, is movable in a vertical dimension, and is tiltable at least generally about a first axis.

24. The medical imaging system of claim 23, wherein said first axis is at least generally horizontally disposed.

25. The medical imaging system of claim 1, further comprising control logic configured to: 1) present a first anatomical image on a first display, wherein said first anatomical image is from a medical procedure currently being executed using said medical system; and 2) simultaneously present a functional identifier on said first display, wherein said functional identifier identifies said corresponding function of a selected said actuator.

* * * * *